(12) United States Patent
Belalcazar et al.

(10) Patent No.: US 8,095,207 B2
(45) Date of Patent: Jan. 10, 2012

(54) IMPLANTABLE MEDICAL DEVICE WITH INTER-ATRIAL BLOCK MONITORING

(75) Inventors: Andres Belalcazar, St. Paul, MN (US); Robert Patterson, Minneapolis, MN (US)

(73) Assignee: Regents of the University of Minnesota, Saint Paul, MN (US)

( * ) Notice: Subject to any disclaimer, the term of this patent is extended or adjusted under 35 U.S.C. 154(b) by 307 days.

(21) Appl. No.: 11/626,329

(22) Filed: Jan. 23, 2007

(65) Prior Publication Data
US 2007/0203420 A1    Aug. 30, 2007

Related U.S. Application Data

(60) Provisional application No. 60/761,160, filed on Jan. 23, 2006.

(51) Int. Cl.
*A61B 5/0402* (2006.01)
(52) U.S. Cl. .................. 600/512; 600/508; 600/509
(58) Field of Classification Search .............. 607/14, 607/17, 27, 9; 600/514, 509
See application file for complete search history.

(56) References Cited

U.S. PATENT DOCUMENTS

| | | | | |
|---|---|---|---|---|
| 5,520,191 | A * | 5/1996 | Karlsson et al. | 600/515 |
| 5,803,084 | A * | 9/1998 | Olson | 600/512 |
| 5,810,739 | A * | 9/1998 | Bornzin et al. | 600/510 |
| 6,073,046 | A * | 6/2000 | Patel et al. | 600/509 |
| 6,668,194 | B2 | 12/2003 | VanHout | |
| 6,760,615 | B2 * | 7/2004 | Ferek-Petric | 600/518 |
| 7,424,321 | B2 * | 9/2008 | Wariar et al. | 600/514 |
| 7,751,875 | B2 * | 7/2010 | Bojovic et al. | 600/512 |
| 2002/0143368 | A1 * | 10/2002 | Bakels et al. | 607/9 |
| 2003/0014084 | A1 | 1/2003 | VanHout | |
| 2003/0060851 | A1 | 3/2003 | Kramer et al. | |
| 2003/0083587 | A1 * | 5/2003 | Ferek-Petric | 600/512 |
| 2006/0235322 | A1 * | 10/2006 | Simske et al. | 600/512 |

OTHER PUBLICATIONS

Abraham, "P-wave analysis in myocardial infarction, pulmonary edema, and embolism," *Am. Heart J.*, 1975, 89:301-304.
Ariyarajah et al., "Correlation of Left Atrial Size With P-Wave Duration in Interatrial Block," *Chest*, 2005, 128:2615-2618.
"Atrial and Ventricular Depolarization Changes," American Heart Association, Nov. 12, 2005, website, 5 pages, www.americanheart.org/presenter.jhtml?identifier=563.
"Cardiac Conduction System," American Heart Association, Nov. 12, 2005, website, 3 pages, www.americanheart.org/presenter.jhtml?identifier=68.
"ECG scribbles," website, Nov. 12, 2005, 26 pages, www.anaesthetist.com/icu/organs/heart/ecg/.
Jin et al., "Significance of electrocardiographic isolated abnormal terminal P-wave force (left atrial abnormality). An echocardiographic and clinical correlation," *Arch. Internal Med.*, 1988, 148(7).

(Continued)

*Primary Examiner* — Niketa Patel
*Assistant Examiner* — Joseph Stoklosa
(74) *Attorney, Agent, or Firm* — Fish & Richardson P.C.

(57) ABSTRACT

An implantable medical device includes a voltage measurement circuit to measure a potential difference between implanted electrodes in a thorax of a living being, the potential difference resulting from an electrical P-wave cardiac signal. The implantable medical device also includes a processing unit to calculate a vector corresponding to the P-wave cardiac signal, the vector comprising a magnitude and a direction, and derived from measured potential differences and orientations defined by locations of the implanted electrodes. The implantable medical device further includes a monitoring unit to track a rotation of the vector corresponding to the P-wave cardiac signal. In various implementations, the monitoring unit may use the rotation to detect an inter-atrial block condition.

10 Claims, 13 Drawing Sheets

OTHER PUBLICATIONS

Klabunde, "Cardiovascular Physiology Concepts," website, 2 pages, Nov. 12, 2005, www.cvphysiology.com/Arrhythmias/A009.htm.

Romhilt and Scott, "Left atrial involvement in acute pulmonary edema," *Am. Heart J.*, 1972, 83:328-331.

* cited by examiner

| | Initial Late P-Wave Voltage | Voltage After Rotation (mV) | Voltage Change (mV) |
|---|---|---|---|
| | 180 | 182 | 184 |
| 1) Can to SVC Coil | 0.2501 | 0.3143 | 0.0642 |
| 2) Can to Right Atrium | 0.2862 | 0.4919 | 0.2057 |
| 3) Can to Right Ventricle Coil | -0.668 | 0.2347 | 0.3015 |
| 4) Can to Right Ventricle Tip | -0.1086 | 0.1286 | 0.2372 |
| 5) Can to Left Ventricle | -0.3072 | -0.2393 | 0.0679 |
| 6) Left Ventricle to Right Ventricle Coil | 0.2404 | 0.4741 | 0.2337 |
| 7) Left Ventricle to Right Atrium | 0.5934 | 0.7313 | 0.1379 |
| 8) Left Ventricle to Right Ventricle Tip | 0.1986 | 0.3679 | 0.1693 |
| 9) Left Ventricle to SVC Coil | 0.5573 | 0.5537 | -0.0036 |
| 10) Right Ventricle Tip to SVC Coil | 0.3587 | 0.1857 | -0.173 |

FIG. 6

IMPLANTABLE MEDICAL DEVICE WITH INTER-ATRIAL BLOCK MONITORING

CROSS REFERENCE TO RELATED APPLICATIONS

This application claims priority from U.S. Provisional Patent Application Ser. No. 60/761,160, filed Jan. 23, 2006, and titled "Implantable Medical Device with Inter-Atrial Block Monitoring," which is incorporated by reference in its entirety.

TECHNICAL FIELD

The description relates to monitoring cardiac signals in a living being for the detection of cardiac anomalies.

BACKGROUND

With an aging population, cost-effective patient management of chronic heart disease is a high priority for today's medical device industry. In particular, pacemaker companies are increasingly interested in adding sensors and monitors to their implantable devices. For example, the United States Food and Drug Administration (FDA), which regulates medical devices, recently approved an implantable defibrillator that uses measured impedance to monitor edema, a pathology associated with advanced heart failure. If a heart failure patient decompensates (meaning that normal fluid balance is lost as a result of poor ventricular function, causing fluid backup in the venous systems), edema may develop in the lungs and tissues. The device may provide advanced warnings, and therefore allow for opportune corrective interventions. Costly hospitalizations may thus be avoided.

It is known that the conventional twelve-lead electrocardiogram (ECG), externally recorded with skin electrodes attached externally to a patient's skin, displays variations when there are abnormalities of the left atrium, one of the four chambers of the heart. This ECG variation has been referred to as "left atrial abnormality," or "left atrial enlargement." Cardiology textbooks describe an association of this finding with enlargement of, or high blood pressures within, the left atrium, as well as with electrical conduction defects between the right atrium and the left atrium of the heart. Several studies have established the relation of the left atrial abnormality to edema and decompensation in heart failure.

One study investigated the relationship between lung edema clearance and the ECG variation, measured in the study using a quantity known as "PTF-V1," which refers to the electrocardiographic force of the terminal P-wave, as monitored in lead V1. The electrocardiographic force is known to be estimated by multiplying the duration of the ECG wave in question by its amplitude. In the study, patients who were in pulmonary edema initially presented with ECG (PTF-V1) more negative than −0.03 mm-secs. When the patients were treated and their pulmonary edema relieved, the PTF-V1 magnitude on the ECG dropped significantly. This finding provides motivation for using this variation of the ECG as a marker for edema. Later investigation established that the true mechanism for the ECG PTF-V1 finding is a condition known as inter-atrial block. This condition occurs when the activation of the left atrium lags abnormally in time with respect to the right atrium. The term "block" denotes an abnormal delay of the normal right to left conduction in the atria.

FIG. 1 shows conventional twelve-lead ECG traces 2, 4, externally recorded with conventional skin electrodes for a patient suffering from inter-atrial block. The Lead II trace 2 shows a widened P-wave 6 with a notch 8 at a location where a peak of the P-wave 6 should be, caused by an abnormally delayed activation of the left atrium with respect to the right atrium. This notch 8 is indicative of inter-atrial block, in contrast to a P-wave of a healthy patient, which would not include a significant notch. The Lead V1 trace 4 also shows a P-wave 10 that has a pronounced negative trough 12, indicative of inter-atrial block. This negative trough 12 develops in the second half of the P-wave, referred to as the terminal P-wave. Because of these ECG changes, this abnormality is also referred to as a rotation of the terminal part of the P-wave cardiac vector. The development of a larger negative voltage in lead V1 implies a more posterior and left direction of that cardiac vector.

Present medical knowledge contemplates that this inter-atrial block is secondary to fluid overload (as in thoracic edema) stressing the left atrium, either by enlarging it or straining it with high pressure. An enlarged left atrium also poses risks for atrial fibrillation, an undesirable cardiac arrhythmia, as well as an enhanced risk for dangerous blood clots (i.e., systemic embolisms).

Because a conventional ECG is administered by a physician at a medical facility, the patient must ordinarily schedule an appointment for the procedure and submit to the examination at the medical facility. Moreover, the conventional ECG captures an indication of cardiac activity over only a small, finite time interval. As such, a patient in the early stages of inter-atrial block may elude detection by conventional ECG monitoring techniques because the disease may progress following the initial examination. It would be desirable to periodically monitor for the inter-atrial block condition twenty-four hours a day. Patients with such a monitor could be warned of an impending edema decompensation, or of the appearance of an undesirable atrial fibrillation precursor.

One way to monitor for inter-atrial block is to measure the conduction time between the activation of the left atrium and the right atrium. This can be measured in a catheter lab, and can also be done using an implanted medical device, such as a pacemaker or defibrillator. FIG. 2a is a diagram of a human heart 30 with implanted electrodes and leads. Right atrium electrodes 32 are located in a right atrium 34 of the heart 30, coronary sinus electrodes 36 are located in a coronary sinus 38 (shown in dashed lines) of the heart 30, and coronary vein electrodes 40 are located in coronary veins over a left ventricle 42 of the heart 30. The right atrium electrodes 32 are attached to a right atrium lead 44, and the coronary sinus electrodes 36 and coronary vein electrodes 40 are attached to a left ventricular lead 46.

FIG. 2b is a view of a right atrium electrogram trace 50 and a left atrium electrogram trace 52. The right atrium electrogram trace 50 can be measured using the right atrium electrodes 32, and corresponds primarily to that portion of the electrical cardiac P-wave associated with the right atrium. As such, the right atrium electrogram trace 50 indicates when the right atrium activates. The left atrium electrogram trace 52 can be measured by the coronary sinus electrodes 36, and corresponds primarily to that portion of the P-wave associated with the left atrium, thus indicating when the left atrium activates. An inter-atrial delay 54 can be measured between common points of the right atrium electrogram trace 50 and the left atrium electrogram trace 52, and this delay 54 can be monitored over time. In FIG. 2b, the inter-atrial delay 54 is measured between peaks of the electrogram traces 50, 52.

However, using an implanted medical device to measure activation delays accurately requires a nonstandard lead arrangement, such as using a multipolar coronary sinus lead, which poses mechanical challenges (e.g., connectors, feedthroughs and attendant size and complexity that they introduce, along with concerns related to lead fatigue resistance and lead diameter). Requiring a multipolar coronary sinus lead may exclude patients receiving a device upgrade or replacement (due to battery exhaustion, for example). Additionally, adding electrodes to standard leads can be difficult because the industry may be resistant to change.

SUMMARY

In a first general aspect, an implantable medical device includes a voltage measurement circuit to measure a potential difference between implanted electrodes in a thorax of a living being, the potential difference resulting from an electrical P-wave cardiac signal. The implantable medical device also includes a processing unit to calculate a vector corresponding to the P-wave cardiac signal, the vector comprising a magnitude and a direction, and derived from measured potential differences and orientations defined by locations of the implanted electrodes. The implantable medical device further includes a monitoring unit to track a rotation of the vector corresponding to the P-wave cardiac signal. In various implementations, the monitoring unit may use the rotation to detect an inter-atrial block condition.

In another general aspect, an implantable medical device includes a voltage measurement circuit to measure a potential difference between implanted electrodes in a thorax of a living being, where the potential difference results from an electrical P-wave cardiac signal. The implantable medical device also includes a processing unit to calculate an inter-atrial block value based on changes in the measured potential difference.

In yet another general aspect, a method of monitoring cardiac pathologies in a human being includes measuring a first vector associated with an electrical P-wave cardiac signal using one or more implanted electrode pairs within the heart. The method also includes measuring a second vector associated with an electrical P-wave cardiac signal using the one or more implanted electrode pairs. The method further includes calculating a rotation value by comparing the second vector to the first vector, and using the rotation value to estimate fluid decompensation of the human being.

In yet another general aspect, a method of detecting fluid decompensation in a human being includes implanting a first electrode pair within the human being, the first electrode pair including a first electrode and a second electrode, and where a relative location of the first electrode to the second electrode defines a first orientation. The method also includes implanting a second electrode pair within the human being, the second electrode pair comprising a third electrode and a fourth electrode, and where a relative location of the third electrode to the fourth electrode defines a second orientation. The method further includes determining a first component vector by measuring a first voltage between the first and second electrodes and using the first orientation, the first component vector associated with an electrical cardiac event, and determining a second component vector by measuring a second voltage between the third and fourth electrodes and using the second orientation, the second component vector associated with the electrical cardiac event. The method further includes determining a resultant vector by combining the first and second component vectors. The method further includes determining a degree of fluid decompensation of the human being by tracking changes in the resultant vector.

In various implementations, the method may include determining the degree of fluid decompensation by tracking a magnitude of the resultant vector. A direction of the resultant vector may also be tracked to determine the degree of fluid decompensation.

Advantages of the techniques disclosed in this document may include one or more of the following: an inter-atrial block condition may be detected, measured, and monitored twenty-four hours per day, 365 days per year. Patients may be advantageously warned of an impending edema decompensation, or of an appearance of an undesirable cardiac arrhythmia or atrial fibrillation precursor, or of dangerous blood clots, or of heart failure.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 6 is a table of computer-modeled simulation results showing voltages associated with P-vector rotation for various measurement electrode-pair combinations.

Like reference symbols in the various drawings indicate like elements.

DETAILED DESCRIPTION

Figure 1:
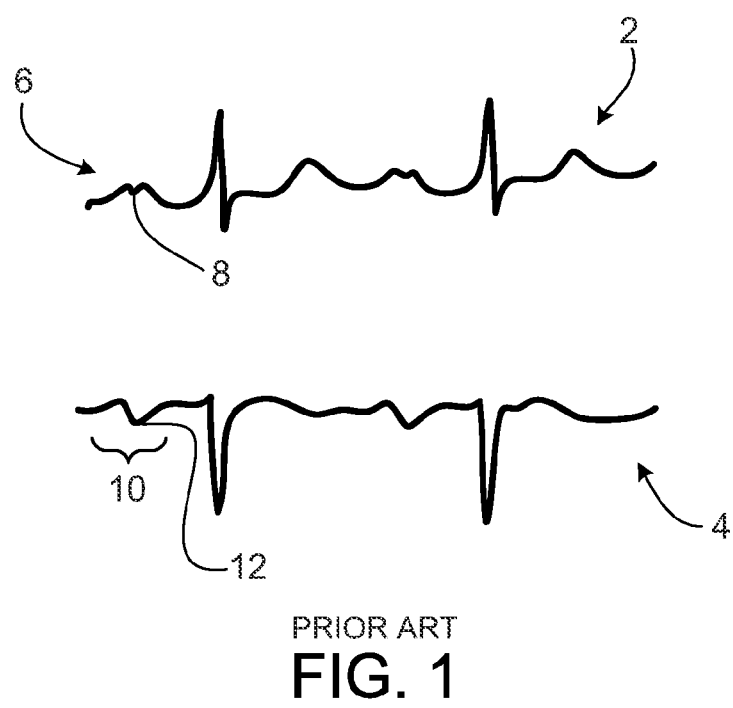
FIG. 1 shows prior art twelve-lead ECG signals, externally recorded with skin electrodes, for a patient suffering from inter-atrial block.
Figure 2A:
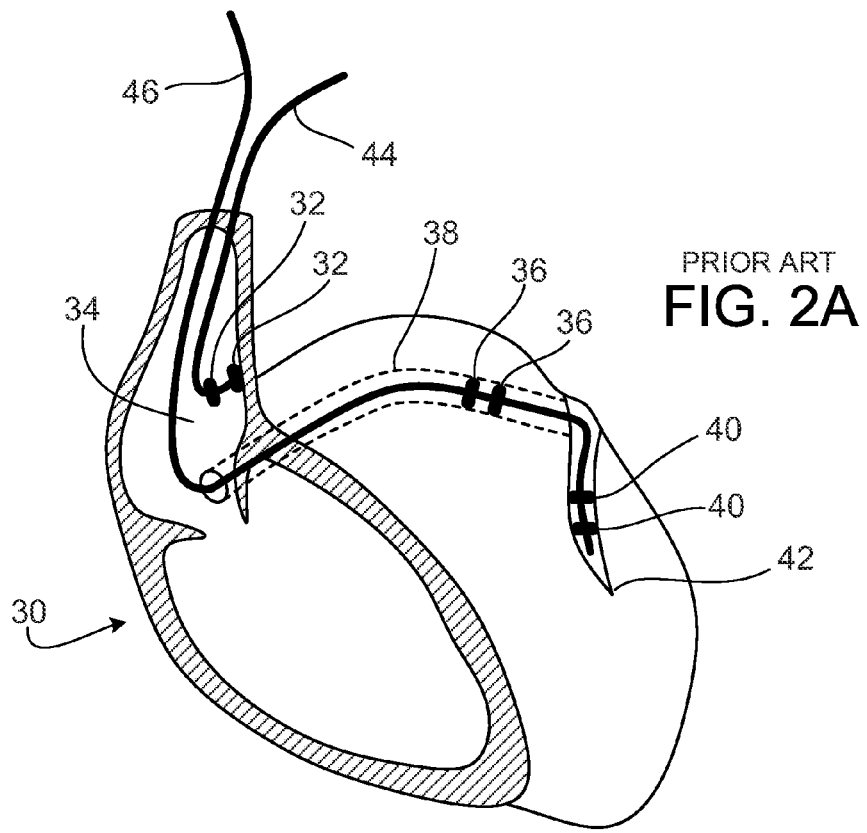
FIG. 2a is a prior art diagram of a human heart with implanted electrodes and leads.
Figure 2B:
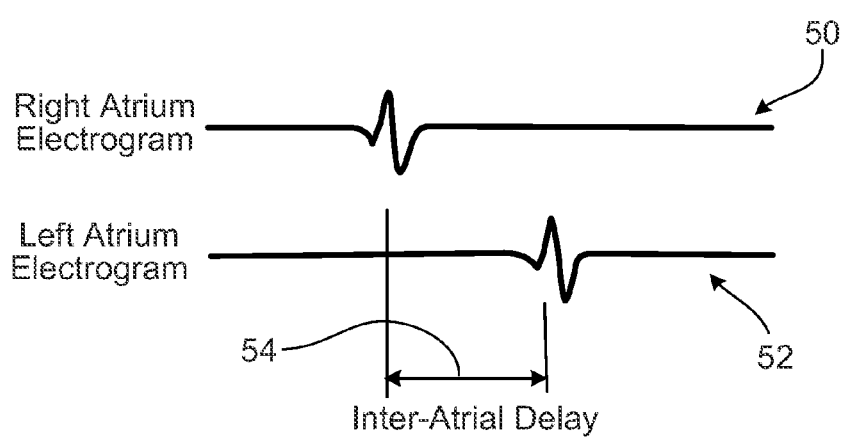
FIG. 2b is a prior art view of a right atrium electrogram trace and a left atrium electrogram trace.
Figure 3:
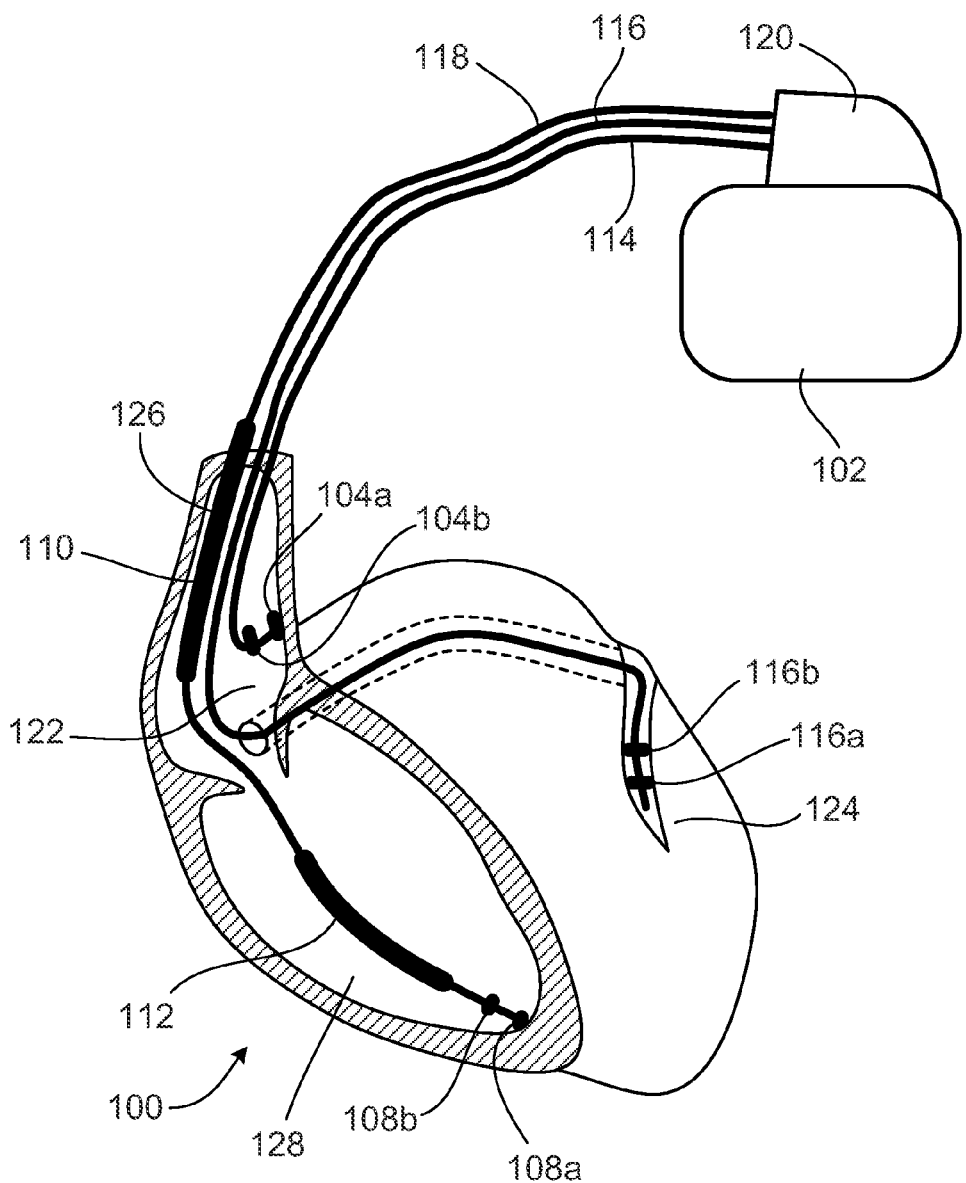
FIG. 3 is a perspective diagram of a human heart and an implantable medical device that is connected to implanted electrodes and defibrillation coils via implanted leads.

FIG. 3 is a perspective diagram of a human heart 100 and an implantable medical device 102 that is connected to implanted electrodes 104, 106, 108 and defibrillation coils 110, 112 via implanted leads 114, 116, 118. The implantable medical device 102 may be sized for implantation in a chest region of a patient, and may be a pacemaker or defibrillator. The implantable medical device 102 includes a monitoring circuit for detecting and monitoring an inter-atrial block condition, atrial fibrillation, edema, and heart disease, and for predicting patient decompensation in response to the detection and monitoring. The implantable medical device 102 includes a port 120, into which a right atrial lead 114, a left ventricular lead 116, and a right ventricular lead 118 may attach. The leads 114, 116, 118 may electrically connect the implanted medical device 102 to various sensors positioned within the heart 100 or in a thorax or neck of the patient.

Right atrium electrodes 104 are attached to the right atrial lead 114, and are positioned in a right atrium 122 of the heart 100. In the implementation shown in FIG. 3, the right atrium electrodes 104 are shown as a tip electrode 104a and a ring electrode 104b, but other combinations are possible. Coronary vein electrodes 106 are attached to the left ventricular lead 116 and positioned in coronary veins that cover a left ventricle 124 of the heart 100. The coronary vein electrodes 106 are shown as a distal coronary vein electrode 106a and a proximal coronary vein electrode 106b, referring to their location on the left ventricular lead 116 with respect to the implantable medical device 102. An SVC coil 110 is positioned in a superior vena cava (SVC) 126 and attached to the right ventricular lead 118. Also attached to the right ventricular lead 118 are right ventricle electrodes 108 and a right ventricular coil 112, each of which are located in a right ventricle 128 of the heart 100. In this illustrative implementation, the right ventricle electrodes 108 are shown as a tip electrode 108a and a ring electrode 108b. In other implementations, one or more of the electrodes shown in FIG. 3 may be omitted from the configuration, such as one of the coronary vein electrodes 106 or one of the right ventricle electrodes 108 (e.g., the right ventricular ring electrode 108b). Unipolar leads may also be used. The implantable medical device 102 may further include one or more electrodes on an external device surface to be used in measurements, which electrodes may be referred to as "can" or "header" electrodes.

Figure 4:
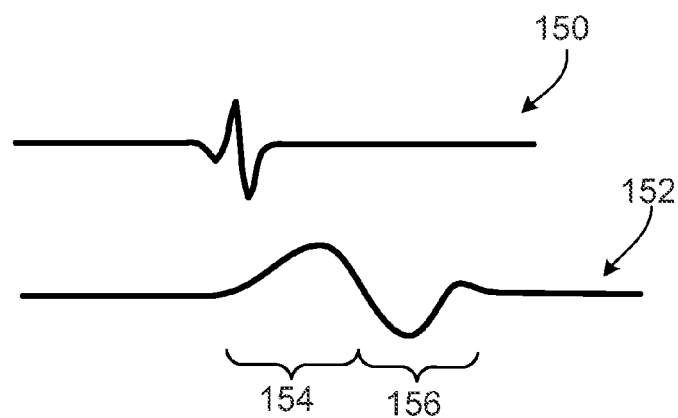
FIGS. 4-5 are views of a right atrium electrogram and a wideband electrogram.

FIG. 4 is a view of a right atrium electrogram 150 and a wideband electrogram 152. The right atrium electrogram 150 may be recorded with the right atrium electrodes 104 (FIG. 3), and includes information primarily associated with electrical activity in the right atrium 122. The right atrium electrogram 150 may be measured using a narrowband amplifier circuit located within the implantable medical device 102. The wideband electrogram 152 contains far-field information associated with electrical activity in both the right atrium 122 and the left atrium. The wideband electrogram 152 contains information primarily corresponding to electrical activity of the right atrium 122 in a first phase 154 of the wideband electrogram 152, and contains information primarily corresponding to electrical activity of the left atrium in a second phase 156 of the wideband electrogram 152. The second phase 156 of the wideband electrogram is known as the terminal P-wave. Taken together, the first phase 154 and second phase 156 of the wideband electrogram 152 comprise the P-wave electrical cardiac signal, including measurements of atrial activation activity. The wideband electrogram 152 may be measured with a wideband amplifier circuit located within the implantable medical device 102, for example. In some implementations, an amplifier circuit within the implantable medical device 102 may be programmed with differing filter values such that either a wideband or narrowband amplifier circuit is realized, depending on the application.

In one implementation, a narrowband response may be defined as that centered at around 40 Hz with sidebands of 10 to 20 Hz in width. This frequency response design may be used to capture localized (as opposed to far-field) electrical activity of the heart, conventionally recorded with closed-spaced electrodes. In an implementation, a wideband electrogram may be recorded using amplifiers with frequency responses of 4-15 Hz, 4-50 Hz, or 2-50 Hz. Other frequency responses may also be used. These responses may be used to record global electrograms that reflect broader and farther electrical activity of the heart's muscles, and hence may be referred to as far-field or wideband electrograms. The lower frequency range may ensure that the slower P-waves are adequately recorded.

Figure 5:
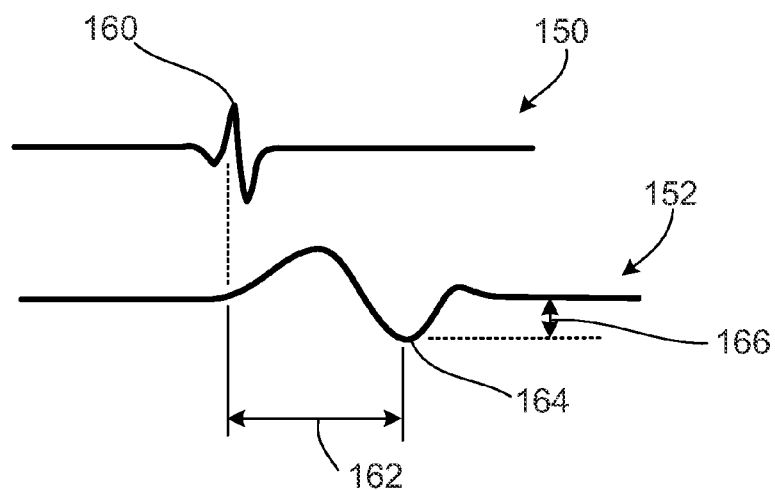

In one implementation, the implantable medical device senses the right atrium electrogram 150 and initiates a timer. The timer may count for a predetermined time interval, after which a voltage measurement circuit within the implantable medical device 102 may measure a potential difference (voltage) between a pair of electrodes and may use the measured voltage to assess inter-atrial block. FIG. 5 shows the right atrium electrogram 150 and the wideband electrogram 152 from FIG. 4. A sense circuit within the implantable medical device 102 may detect a feature 160 of the right atrium electrogram 150, and may initiate a timer to count for a predetermined time interval 162. For example, the sense circuit may use a comparator with a threshold value (predetermined fixed or adaptive) to monitor the signal 150 in relation to the threshold value. In the implementation shown in FIG. 5, the predetermined time interval 162 begins at a peak 160 of the right atrium electrogram 150 and ends at a negative trough 164 of the wideband electrogram 152. A timer interval value can be set by a physician at the time of implantation, and may be adjusted later, such as by using telemetry to update the value. When the time interval 162 elapses, the voltage measurement circuit may measure the depth 166 of the negative trough 164 of the terminal P-wave by measuring a voltage between two implanted electrodes.

Several combinations of electrodes are possible. For example, the voltage may be measured between the can electrode and the SVC coil 110, between the can electrode and one of the right atrium electrodes 104, between the can electrode and the right ventricle coil 112, between the can electrode and the right ventricle tip electrode 108a, between the can electrode and one of the coronary vein electrodes 106, between one of the coronary vein electrodes 106 and the right ventricle coil 112, between one of the coronary vein electrodes 106 and one of the right atrium electrodes 104, between one of the coronary vein electrodes 106 and one of the right ventricle electrodes 108 (such as the right ventricle tip electrode 108a), between one of the coronary vein electrodes 106 and the SVC coil 110, or between one of the right ventricle electrodes 108 and the SVC coil 110.

FIG. 6 is a table of computer-modeled simulation results showing voltages associated with P-vector rotation for various measurement electrode-pair combinations, such as those just described. To obtain the voltages using the simulation technique, a three-dimensional computer model obtained with Magnetic Resonance Imaging may divide the human thorax into many small volumes, each corresponding to body tissue. Each small tissue volume may be assigned an appropriate electrical resistivity (e.g., blood=150 ohms-cm, lung=1400 ohms-cm, muscle=400 ohms-cm, etc.) according to published tables. Electrical current injection can be introduced at various locations in the thorax to simulate cardiac activity, such as a left atrial depolarization, or terminal P-wave. Measurement electrodes may then be placed at other various locations in the model to simulate, for instance, pacemaker or defibrillator cardiac electrodes. The computer may then calculate the resulting voltage potentials at each of the small volumes of the thorax using electric field equations. The current injection locations simulating the terminal P-wave may then be varied to simulate the vector rotation that occurs with a diseased state of inter-atrial block. Measurements may then be taken at the same voltage electrodes, thus permitting simulation of voltage changes due to the disease.

Figure 7:
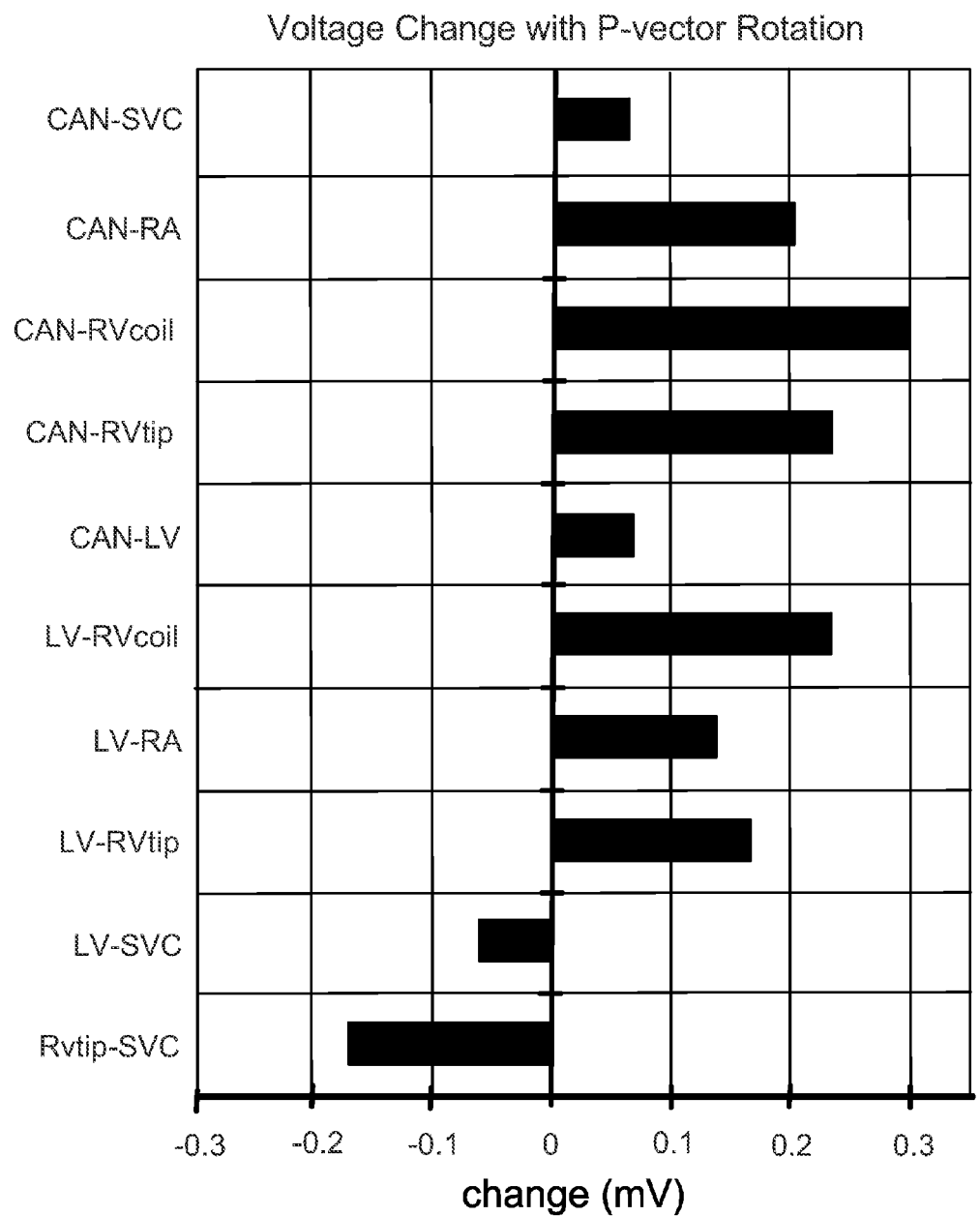
FIG. 7 is a chart of the simulation results from FIG. 6.

In this way, FIG. 6 shows, for the various measurement electrode configurations, the change in measured voltage (in millivolts) in a patient, before and after developing inter-atrial block. A first column 180 shows an initial P-wave voltage simulated for each of the configurations. These voltages correspond to a P-wave voltage in a normal state. A second column 182 shows a simulated voltage after developing inter-atrial block and its associated P-wave rotation, for each of the configurations. A result column 184 shows the difference in simulated voltage between the diseased state and the healthy state. Values in the result column were calculated by subtracting values in the first column 180 from those in the second column 182, respectively, for each of the configurations. For example, for the Can to Right Ventricle Coil configuration 186, a P-wave voltage difference of 0.3015 mV was simulated; for the Left Ventricle to Right Ventricle Coil configuration 188, a P-wave voltage difference of 0.2337 mV was simulated; for the Left Ventricle to Right Atrium configuration 190, a P-wave voltage difference of 0.1379 mV was simulated; for the Left Ventricle to Right Ventricle Tip configuration 192, a P-wave voltage difference of 0.1693 mV was simulated; and for the Right Ventricle Tip to SVC Coil configuration 194, a P-wave voltage difference of −0.1730 mV was simulated. FIG. 7 is a chart of the simulation results from FIG. 6.

Figure 8:
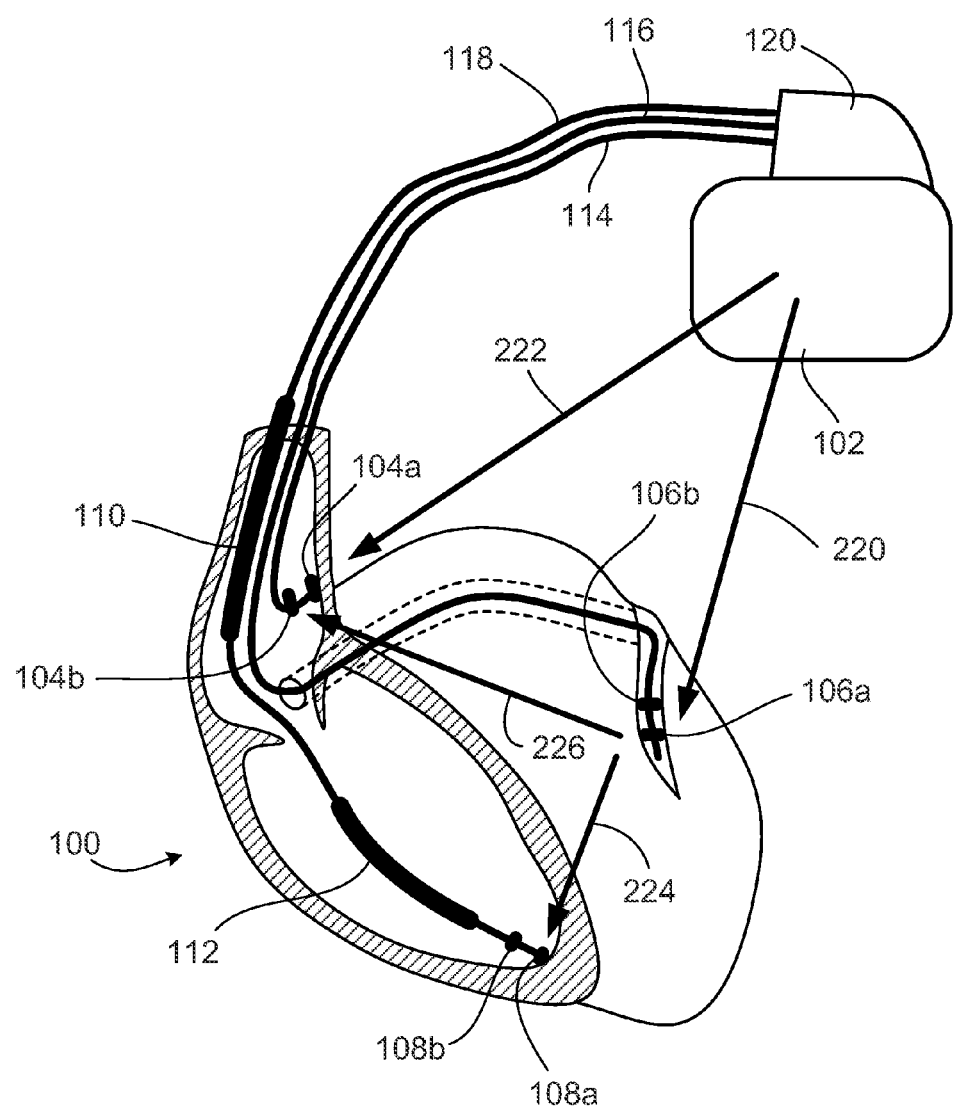
FIG. 8 is a perspective diagram of the human heart and implantable medical device and sensors of FIG. 3, and vector orientations for component P-wave vector measurements.

The description above describes monitoring in one dimension, on one orientation. Other implementations may use more than one measurement to calculate a P-wave vector in two or three dimensions, and may track the P-wave vector over time to monitor rotation of the P-wave vector, which may be indicative of, or a precursor for, an inter-atrial block condition, atrial fibrillation, edema, or heart disease. FIG. 8 is a perspective diagram of the human heart 100 and implantable medical device 102 and sensors 104, 106, 108, 110, 112 of FIG. 3, and vector orientations for component P-wave vector measurements. A precise implanted electrode location and angular orientation with respect to other electrodes can be determined after implantation using X-ray frontal and lateral images, and this information can be transmitted to the implantable medical device 102. In some implementations, the implantable medical device 102 may calculate the angular orientations (for example, by using the X-ray data), while in other implementations this information may be externally determined and supplied to the device 102 (as by wireless telemetry). Alternatively, estimations of electrode location and respective angular orientations may be used. Using this information, the monitoring circuit within the device 102 may define coordinate axes for component P-wave vector computations, based on the relative locations of chosen electrode pairs.

A component P-wave vector axis, or orientation, may be defined by any two of the electrodes 104a, 104b, 106a, 106b, 108a, 108b, 110, 112, and a potential difference may likewise be measured between any two of the electrodes 104a, 104b, 106a, 106b, 108a, 108b, 110, 112. For example, a Can-LV orientation 220 may be defined between the can or header electrode (located on an external surface of device 102) and one of the coronary vein electrodes 106 (such as a distal coronary vein electrode 106a). Similarly, a Can-RA orientation 222 may be defined between the can or header electrode and one of the right atrium electrodes 104 (e.g., 104a or 104b). An LV-RVtip orientation 224 may be defined between one of the coronary vein electrodes 106 (such as the proximal coronary vein electrode 106b) and one of the right ventricle electrodes 108 (such as the right ventricle tip electrode 108a), and an LV-RA orientation 226 may be defined between one of the coronary vein electrodes 106 and one of the right atrium electrodes 104. For clarity, FIG. 8 only shows four orientations, but additional or alternative orientations could similarly be defined for each of the configurations shown in the table of FIG. 6 and the chart of FIG. 7 and described above. For example, a Can-RVtip orientation could be defined from the can or header electrode to the right ventricle tip electrode 108a.

In an implementation, the monitoring circuit may select two orientations to define a two-dimensional plane. Then, the monitoring circuit may measure P-wave vector voltages across each of the electrode pairs defining the selected orientations, and may use the measured voltages and selected orientations to calculate a P-wave vector component in the defined plane, including both magnitude and direction. This information could be stored in memory in the implantable medical device 102, or could be transmitted to an external monitoring station. The measurements could then be periodically repeated and the P-wave vector component in the defined plane similarly calculated, and the monitoring circuit could track P-wave vector component rotation on the plane over time by comparing the present vector to the vector as previously measured. The monitoring circuit may use this magnitude and direction information to predict, detect, and monitor an inter-atrial block condition, atrial fibrillation, edema, or heart disease. A warning flag may be set in device memory or transmitted to an external monitoring station, for example, to indicate that an inter-atrial block condition has been detected, or is worsening.

Referring again to FIG. 8, the monitoring circuit may select the Can-RA orientation 222 to represent a first coordinate axis and the LV-RA orientation 226 to represent a second coordinate axis for P-wave vector computations. Taken together, these two orientations 222, 226 may define an approximate coronal or frontal plane in a patient's body. Therefore, measurements taken with those two pairs 222 and 226 may yield a frontal plane component of the P-wave. As an example, if the orientations 222 and 226 form an angle of 60 degrees, and the electrode pair with orientation 222 records a P-wave voltage of 0.766 mV, while the electrode pair with orientation 226 yields 0.939 mV, then the P-wave vector on the frontal plane has a direction of 40 degrees off from direction 222, or 20 degrees from direction 226, and a magnitude of 1 mV. These angles and magnitude may be calculated from the 60 degree separation and the 0.766 mV and 0.939 mV measured components using standard algebra and trigonometry. Similarly, a second pair of orientations 220 and 224 (FIG. 8), given respectively by the Can-LV and LV-RVtip electrode pairs, may define an approximate sagittal (front-to-back) plane in the patient's body, over which P-wave vector rotation (magnitude and direction) on that plane may be tracked using potential difference measurements made between the can electrode and a coronary vein electrode 106, and between a coronary vein electrode 106 and a right ventricle electrode 108.

An extension of the two-dimensional method of monitoring the P-wave vector in one plane may be made to monitor the vector in three-dimensional space. As previously described, taking a first set of two orientations may define a first plane, and voltages may be measured between electrodes defining the orientations to determine a P-wave vector component. A second set of two orientations may be selected to define a second plane, and voltages may similarly be measured between electrodes defining these orientations to determine a P-wave vector component. Then, with the P-wave components determined on each of the first and second planes, a complete determination in three dimensions can be made for the P-wave vector in the thoracic space using the components on the two planes and conventional geometrical projection analysis methods. In an implementation, the first plane and the second plane are not parallel to one another.

In an illustrative implementation of three-dimensional tracking, the monitoring circuit may select orientations to define two planes that are orthogonal or semi-orthogonal to one another using the electrode implant locations, thereby defining a three-dimensional space having an orthogonal or semi-orthogonal coordinate system. For example, the monitoring circuit could select three orientations or four orientations for this purpose. For a frontal plane, orientations 222 and 226 of FIG. 8 may be used, as previously described. A sagittal plane may be obtained from orientations 220 and 224. Thus, in this example, a total of four orientations are selected to form two planes—frontal and sagittal. Then, the monitoring circuit may measure P-wave vector voltages across each of the electrode pairs defining the selected orientations, and may use the measured voltages and selected orientations to calculate P-wave vector components, including P-wave magnitude and P-wave direction, both in the frontal and sagittal planes. Using conventionally known geometry methods, the vector measurements in these two planes may fully resolve the P-wave vector in three dimensions, and the changes in a third horizontal plane determined. This three-dimensional information may be stored in memory in the implantable medical device 102, or may be transmitted to an external monitoring station. The measurements may then be periodically repeated and the P-wave vector similarly calculated, and the monitoring circuit may track P-wave vector rotation over time by comparing the present P-wave vector to the P-wave vector as previously measured. The monitoring circuit may use this information to predict, detect, and monitor an inter-atrial block condition, atrial fibrillation, edema, or heart disease. A warning flag may be set in device memory or transmitted to an external monitoring station, for example. Component P-wave vector measurements may be taken simultaneously, or consecutively within a short time period, such as within about 20 milliseconds.

In another implementation, the monitoring circuit may further incorporate the relative sensitivity of the configurations to P-wave vector rotation, as shown in FIGS. 6-7, into the choice of orientations. For example, the monitoring circuit may use orientations that demonstrate a larger simulated voltage change from a healthy to a diseased state. Orthogonality or semi-orthogonality between orientations is not required, and any combination of the orientations discussed above or shown in FIGS. 6-7 may be used to track P-wave vector rotation. Alternatively, measurements taken between two sensors that define a single orientation may be used to track P-wave magnitude variations over time, which may similarly be used to predict, detect, and monitor an inter-atrial block condition, atrial fibrillation, edema, or heart disease. Magnitude changes in P-wave vectors may also be tracked over time using one or more sensor pairs and may be used to predict and monitor disease.

Figure 9:
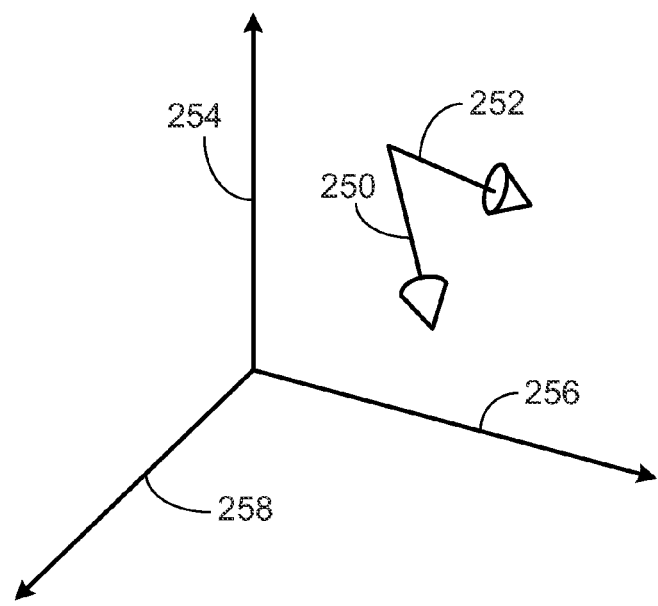
FIG. 9 is a view of an initial P-wave vector and a rotated P-wave vector in three-dimensional space.

FIG. 9 is a view of an initial P-wave vector 250 and a rotated P-wave vector 252 in three-dimensional space. FIG. 9 shows orthogonal coordinate axes defined by a first coordinate axis 254, a second coordinate axis 256, and a third coordinate axis 258. The initial P-wave vector 250 and rotated P-wave vector 252 are shown in the three-dimensional space defined by the coordinate axes 254, 256, 258. As can be seen in FIG. 9, the rotated P-wave vector 252 has rotated posteriorly and laterally with respect to the initial P-wave vector 250, which may be indicative of an inter-atrial block condition. As an example, the first coordinate axis 254 may correspond to the Can-LV orientation 220 (FIG. 8); the second coordinate axis 256 may correspond to the LV-RA orientation 226 (FIG. 8); and the third coordinate axis 258 may correspond to the LV-RVtip orientation 224 (FIG. 8). The monitoring circuit within the implanted medical device 102 may measure P-wave component vectors by making voltage measurements between electrode pairs defining the selected orientations. Resultant P-wave vectors (such as the initial P-wave vector 250 and the rotated P-wave vector 252) may then be calculated using vector computations by combining the P-wave component vectors.

Figure 10:
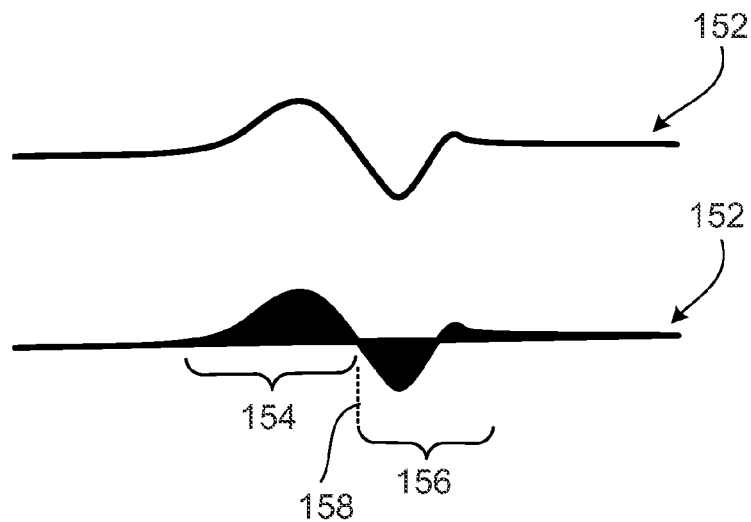
FIGS. 10-11 are views of wideband P-wave electrograms used to determine P-wave vectors.
Figure 11:
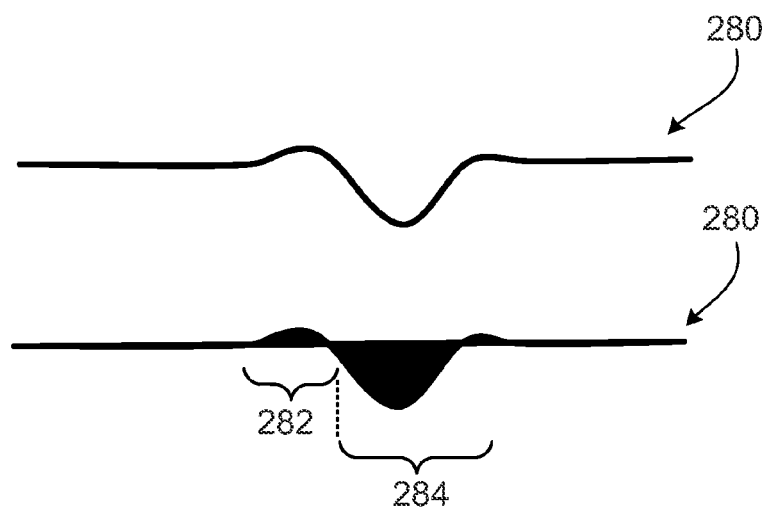

FIGS. 10-11 are views of wideband P-wave electrograms used to determine P-wave vectors. FIG. 10 shows the wideband P-wave electrogram 152 of FIG. 4, which may be measured using one of the sensor configurations described above (such as the Left Ventricle to Right Ventricle Coil configuration 188, see FIG. 6). The electrogram 152 in FIG. 10 corresponds to a healthy patient. The electrogram 152 includes the first phase 154 and the second phase 156 (terminal P-wave) of the P-wave, corresponding primarily to electrical activity in the right atrium and left atrium, respectively. An ECG force may be determined by computing an area defined by the P-wave (that is, the net area above or below the horizontal isoelectric line). Area may be computed by integrating the P-wave over time. As compared to measuring only amplitude, the force may provide an improved and more comprehensive measure of the P-wave vector by providing a better assessment of vector magnitude. The force may be determined with respect to the entire P-wave 152, or may be determined with respect to one or more portions of the P-wave. For example, in one implementation, the area defined by the second phase 156 is used to determine the terminal P-wave vector magnitude. In other implementations, the area defined by both the first phase 154 and the second phase 156 of the P-wave 152 is used to determine the P-wave vector magnitude.

In one implementation, the onset and the offset of the P-wave complex 152 are detected, and a midpoint 158 is computed as the midpoint in time between the onset and offset of the entire P-wave. In FIG. 10, the midpoint 158 is shown where the P-wave becomes negative. The force may be computed by determining the area defined by the P-wave electrogram over the terminal P-wave 156. P-wave onsets and offsets may be calculated using derivatives to determine points of inflection. Alternatively, an R-wave cardiac signal may be detected, and an inflection point and an isoelectric point may be located prior to the R-wave to find the P-wave offset and onset, respectively. FIG. 11 shows a wideband P-wave electrogram 280 for a diseased patient, such as one suffering from an inter-atrial block condition. The diseased P-wave electrogram 280 includes a smaller first phase 282 and an enlarged terminal P-wave section 284, as compared to the healthy patient electrogram 152 (FIG. 10).

Figure 12:
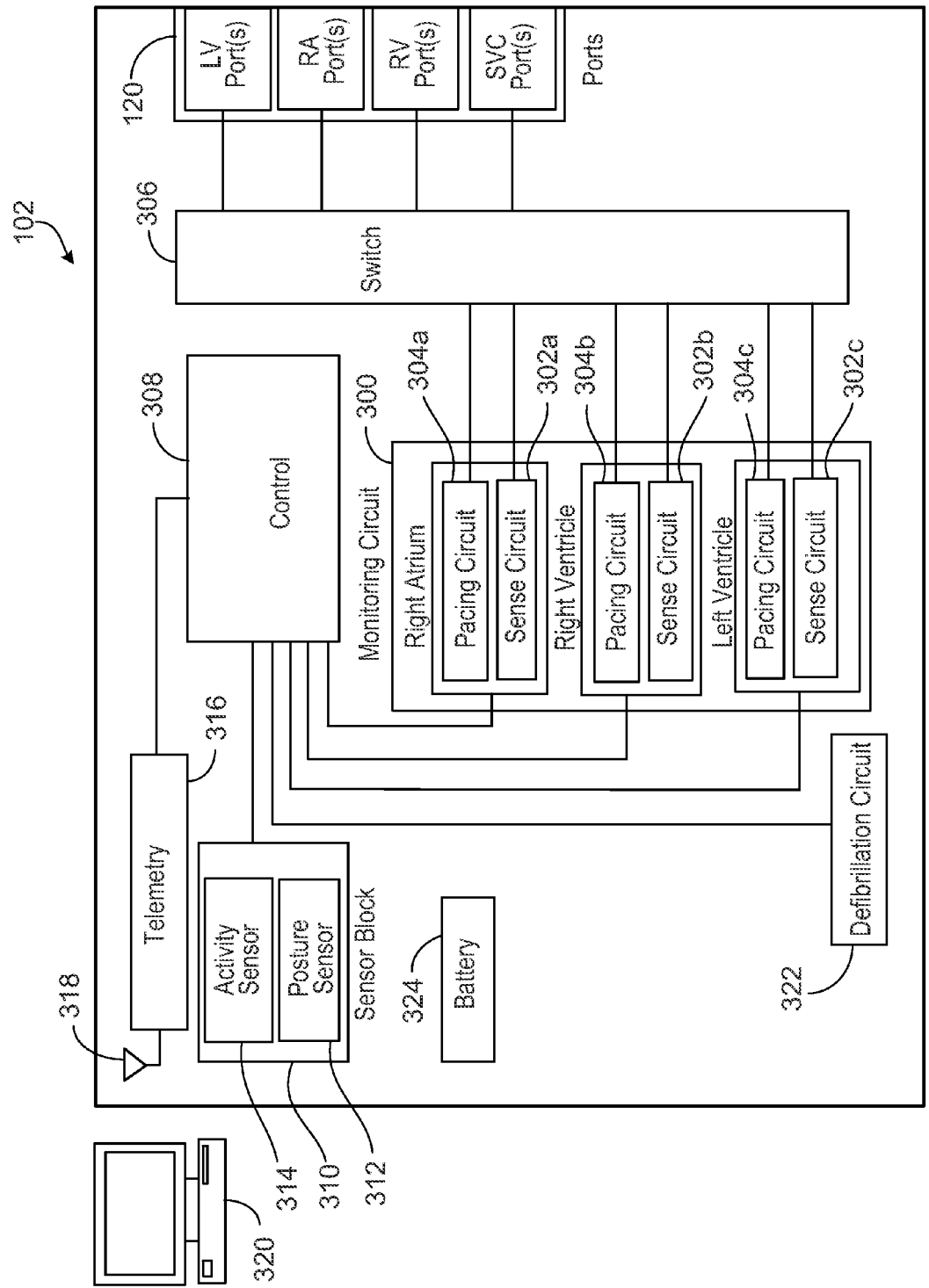
FIG. 12 is a block diagram circuit representation of the implantable medical device from FIGS. 3 and 8.

FIG. 12 is a block diagram circuit representation of the implantable device 102 from FIGS. 3 and 8. Device 102 includes circuits for measuring potential differences and computing P-wave vector magnitudes and directions, and making inter-atrial block assessments, and communication circuits for interfacing with external devices. A monitoring circuit 300 includes one or more sense/measurement circuits 302 and pacing circuits 304. The sense/measurement circuit 302 may include a voltage amplifier that may be used to measure potential differences between any of the implanted electrodes 104, 106, 108, 110, 112, and one or more comparators for use in sensing cardiac events and making voltage comparisons. The voltage amplifier may be programmable, such that appropriate filter values may be used to configure the amplifier as a wideband amplifier or a narrowband amplifier. The pacing circuits 304 may be used to stimulate (pace) cardiac events. While the monitoring circuit 300 shown in FIG. 12 includes three sets of sense/measurement circuits 302 and pacing circuits 304 labeled "Right Atrium," "Right Ventricle," and "Left Ventricle," more or fewer sense/measurement circuits 302 or pacing circuits 304 may be used (such as one, two, four, etc.), and the number of sense circuits 302 need not equal the number of pacing circuits 304. A switch 306 operates in a manner known in the art to permit the sense circuits 302 or pacing circuits 304 to interface with the appropriate port or ports 120, into which the leads 114, 116, 118 may attach.

A control block 308 receives or contains information on the magnitudes of measured voltages. Analog-to-digital (A/D) converters (not shown), within or outside of the control block 308, may be used to translate the information. A processing unit (not shown) such as a microprocessor, microcontroller, or digital signal processor within the control block 308 may then use the voltage information and electrode orientation information to calculate component P-wave vectors. After the component vectors of the P-wave are calculated, the processing unit may combine the component vectors to form a resultant vector. This resultant vector may be the P-wave vector. In some implementations, the control block 308 and processing unit are contained within the monitoring circuit 300. In other implementations, some or all of the components of the monitoring circuit 300 are contained within the control block 308.

The control block 308, as is conventional, may additionally include read-only memory (ROM), random-access memory (RAM), flash memory, EEPROM memory, and the like, which may store instructions that may be executed by the processing unit, as well as digital-to analog (D/A) converters, timers, counters, filters, switches, etc, (not shown). P-wave vector information, inter-atrial block values, and electrode orientation information may also be stored in memory. These control block components may be integrated within a single device, such as an application specific integrated circuit (ASIC), or alternatively may be separate devices. Appropriate busses (not shown) allow communication between components within the control block 308.

Information from a sensor block 310 may be used to adjust the relationship between the measured voltages and the computation of the P-wave vector. A posture sensor 312 may provide patient orientation information to the control block 308, allowing posture compensation to be included in the calculation. Several types of posture sensors could be used, including mercury switches, DC-accelerometers, or other piezoelectric devices. An activity sensor 314, conventionally used to aid in pacing applications, may also provide information to the control block 308. Either sensor 312, 314 may optionally be excluded from the implantable device 102.

A telemetry block 316 may communicate wirelessly using inductive or radio frequency (RF) transmissions over an antenna 318 with a similarly wirelessly equipped external monitoring unit 320. Monitoring unit 320 may be a computer (custom programmer, desktop, laptop, handheld, etc.), a telemedicine home station, a wearable device such as a wristwatch, a mobile phone, or any other appropriate device, and may be used to program the implantable device 102, or to retrieve information from the device 102, such as voltage measurements, P-wave vector information, or inter-atrial block information. This communication link may be used to alert a physician or healthcare provider, for example, such that therapeutic intervention could be promptly initiated. Alternatively, the monitoring unit 320 could utilize a phone connection to dial "9-1-1" and summon an emergency response team, could occasion a similar response by communicating over a network, such as the Internet, or could audibly or textually inform the patient to seek medical attention. In this manner, it is possible to continuously monitor the patient for inter-atrial block, atrial fibrillation, edema, or heart disease twenty-four hours a day, seven days a week, and to alert a physician or care provider promptly in the event of pathology detection. A defibrillation circuit 322 may be used to manage cardiac rhythms. A battery 324 supplies power to the various circuits and blocks of device 102 (for simplicity, connections are not shown in FIG. 12).

Figure 13:
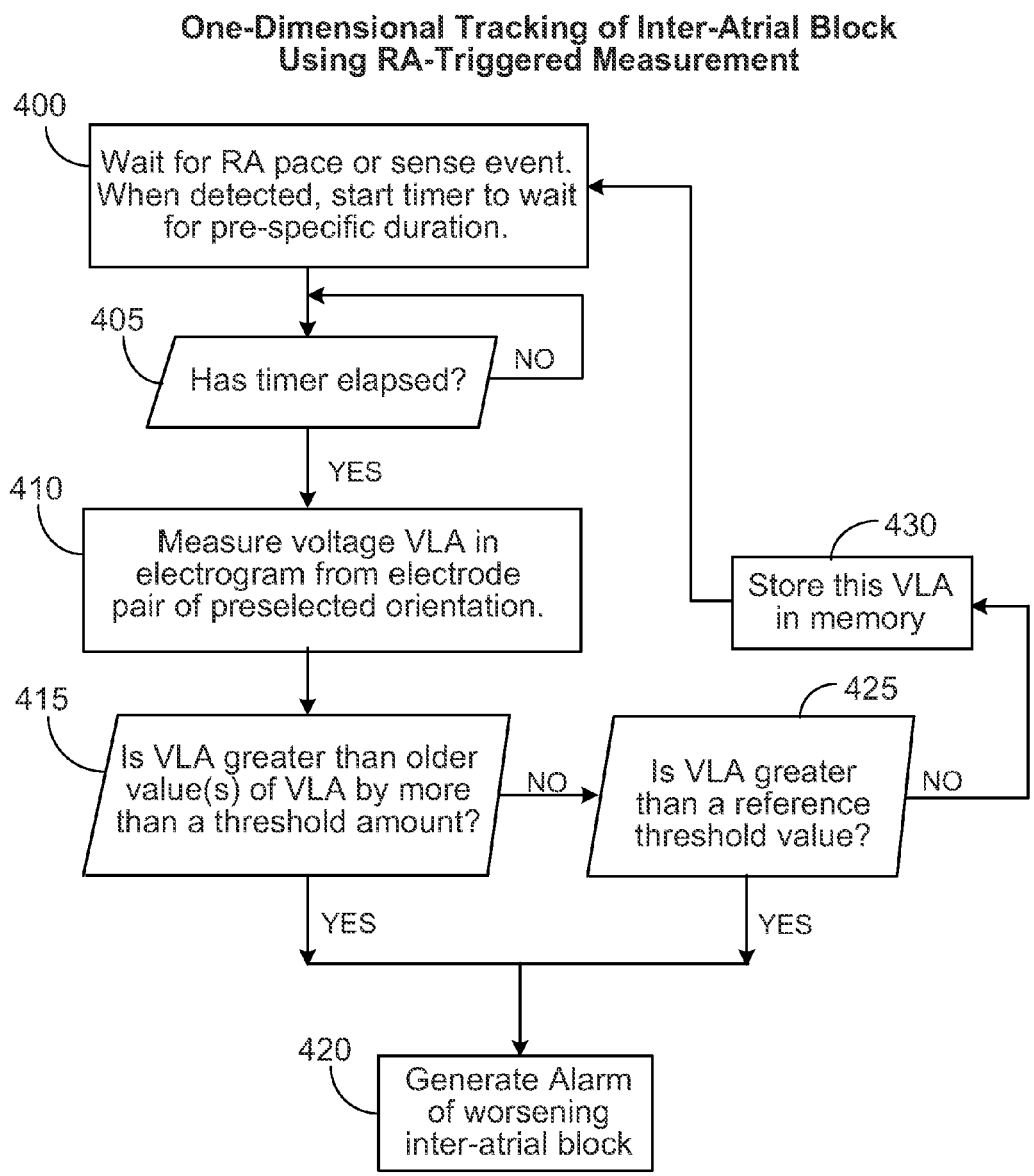
FIG. 13 is a flowchart illustrating an example of how the device of FIG. 12 may track an inter-atrial block condition.

FIG. 13 is a flowchart illustrating an example of how the device 102 of FIG. 12 may track an inter-atrial block condition. The flowchart of FIG. 13 shows an example of how an algorithm may be implemented in the control block 308 of the implantable medical device 102 to track an inter-atrial block condition and trigger a warning indicator if the condition is worsening. The process performed by a control block processing unit executing instructions begins, at step 400, by waiting for a right atrial cardiac event. In an implementation, the right atrial cardiac event may be sensed by a voltage sense amplifier and comparator of sense circuit 302 (FIG. 12); for example, sense circuit 302a may be used to sense the right atrial event. Alternatively, the device 102 may use a pacing circuit 304 (such as pacing circuit 304a) to initiate the right atrial cardiac event.

After detecting the cardiac event, a timer may be initiated to count for a pre-specified time duration. If the duration has elapsed at step 405, a voltage measurement may be taken across electrodes in an electrode pair having a pre-selected orientation (410). In an implementation, a voltage amplifier within one of the sense circuits 302 may be used to measure the voltage. The measured voltage may be labeled "VLA." If the timer has not elapsed at step 405, step 405 may be repeated. Next, after voltage VLA has been measured at step 410, it may be compared to an older measured voltage value at step 415. If VLA is greater than the older value or values of previously measured VLA(s) by more than a threshold amount at step 415, an alarm may be generated, which may indicate a worsening inter-atrial block condition (420). If VLA does not exceed the older value or values of previously measured VLA(s) by more than the threshold amount, the alarm may still be generated (420) if VLA exceeds a reference threshold value at step 425. If not, the present VLA voltage may be stored in memory at step 430, and the process may return to step 400.

Figure 14:
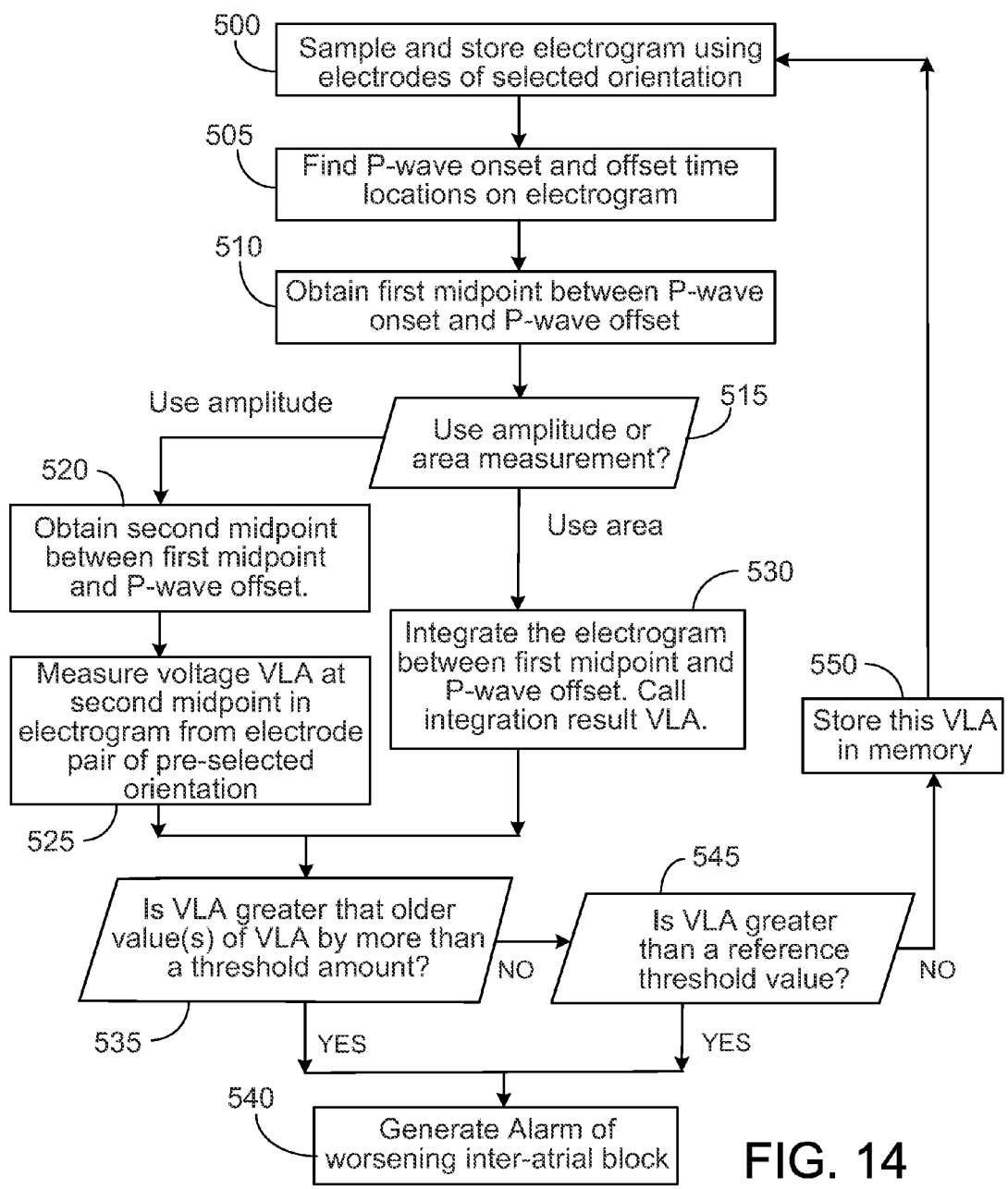
FIGS. 14-15 are flowcharts illustrating examples of how the device of FIG. 12 may track P-wave vector changes and monitor an inter-atrial block condition.
Figure 15:
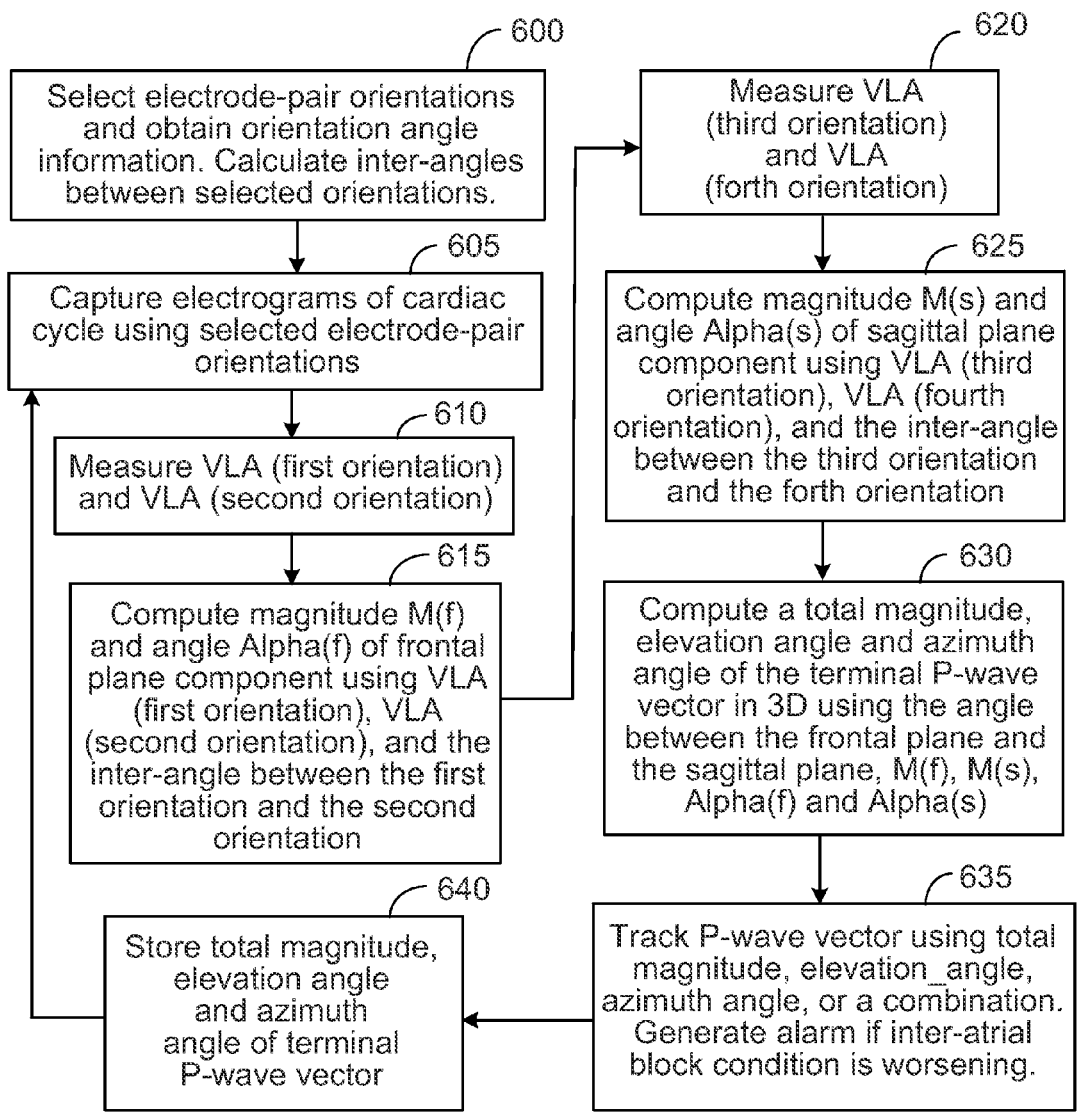

FIGS. 14-15 are flowcharts illustrating examples of how the device 102 of FIG. 12 may track P-wave vector changes and monitor an inter-atrial block condition. The flowchart of FIG. 14 shows an example of how an algorithm may be implemented in the control block 308 of the implantable medical device 102 to track P-wave changes in one dimension using P-wave search measurement. The process performed by a control block processing unit executing instructions begins, at step 500, with sampling and storing an electrogram by making voltage measurements between electrodes in an electrode pair having a selected orientation. In an implementation, an R-wave-to-R-wave cardiac cycle (R-R cycle) may be captured and stored in a memory buffer using a sense/measurement circuit 302 (FIG. 12).

Next, at step 505, P-wave onset and offset time locations may be found on the captured electrogram. In an implementation, the electrogram may be retrieved from the buffer and a right atrial (paced or sensed) cardiac event may be located. A first inflection point, which may correspond to the P-wave onset, may be located on the electrogram within about 50 milliseconds in time prior to the RA-atrial sense event, or within about 50 milliseconds after the RA-pace event (if a pacing circuit was used to initiate the cardiac event). Alternatively, the RA-pace event itself could be used as the onset time of the P-wave. An S-wave or ventricular-pace may then be located on the captured electrogram, and the P-wave offset may correspond to the last inflection point in time prior to the S-wave or ventricular pace. Using the onset and offset points of the P-wave, a first midpoint may be located halfway between the P-wave onset and the P-wave offset points at step 510.

At step 515, either an amplitude measurement or an area measurement may be selected. If an amplitude measurement is selected at step 515, a second midpoint may be obtained on the captured electrogram at a point midway between the first midpoint and the P-wave offset point (520). This second midpoint may be referred to as the "VLA measurement time." Then, at step 525, a voltage may be measured at the second midpoint (VLA measurement time) using electrodes in an electrode pair having pre-selected orientation. This measured voltage may be labeled "VLA." If instead an area measurement is selected at step 515, the captured electrogram may be integrated with respect to time between the first midpoint and the P-wave offset point (530), and the integration result may be labeled "VLA."

At step 535, if VLA is greater than a previously obtained value or values of VLA by more than a threshold amount, an alarm may be generated (540), which may signal that the inter-atrial block condition is worsening. If VLA does not exceed the older value or values of previously measured VLA(s) by more than the threshold amount, the alarm may still be generated (540) if VLA exceeds a reference threshold value at step 545. If not, the present VLA may be stored in memory at step 550, and the process may return to step 500.

The flowchart of FIG. 15 shows an example of how an algorithm may be implemented in the control block 308 of the implantable medical device 102 to track P-wave changes in three-dimensional space. Initially, X-ray images showing implanted electrode locations within a patient's body may be used to calculate orientation angles for defined electrode pair configurations. The process performed by a control block processing unit executing instructions begins, at step 600, with selecting appropriate electrode-pair orientations and obtaining the orientation angle information for the selected orientations. In an implementation, electrode-pair orientations may be selected to approximate a frontal plane and a sagittal plane within the patient's body. For example, the Can-RA orientation 222 (FIG. 8) may be selected as a first orientation; the LV-RA orientation 226 (FIG. 8) may be selected as a second orientation; the Can-LV orientation 220 may be selected as a third orientation; and the LV-RVtip orientation 224 may be selected as a fourth orientation. As described above with regard to FIG. 8, the first and second orientations 222, 226 may define an approximate frontal plane in the patient's body, and the third and fourth orientations 220, 224 may define a define an approximate sagittal plane in the patient's body. The orientation angle information may be transmitted to, or otherwise obtained by, the device 102. Alternatively, orientation angles may be estimated or calculated by other means. An angle between the first orientation 222 and the second orientation 226 may be determined using the respective orientation angles, and may be labeled "inter-angle (frontal plane)." Similarly, an angle between the third orientation 220 and the fourth orientation 224 may be determined using the respective orientation angles, and may be labeled "inter-angle (sagittal plane)."

Next, at step 605, cardiac cycle electrograms may be captured for each of the selected electrode-pair orientations (220, 222, 224 and 226 in this example) using sense/measurement circuits 302. The captured electrograms may be stored in a buffer in memory within the device 102. VLA values for the first orientation 222 and the second orientation 226 may be measured (610), for example, using any of the methods described above with respect to FIG. 13 or FIG. 14. These VLA values may be labeled "VLA (first orientation)," and "VLA (second orientation)," respectively. A magnitude (M(f)) and angle (Alpha(f)) of a frontal plane component of the P-wave vector may then be computed using VLA (first orientation), VLA (second orientation), and inter-angle (frontal plane), at step 615. In like fashion, VLA values for the third orientation 220 and the fourth orientation 224 may be measured (620), and may be labeled "VLA (third orientation)," and "VLA (fourth orientation)," respectively. A magnitude (M(s)) and angle (Alpha(s)) of a sagittal plane component of the P-wave vector may then be computed using VLA (third orientation), VLA (fourth orientation), and inter-angle (sagittal plane), at step 625.

Having computed magnitude and angle for both the frontal P-wave component vector and the sagittal P-wave component vector, a total magnitude, elevation angle and azimuth angle of the terminal P-wave vector in three-dimensional space may be computed, at step 630, using M(f), M(s), Alpha(f), Alpha(s), and the angle between the frontal plane (defined by the first and second orientations 222, 226) and the sagittal plane (defined by the third and fourth orientations 220, 224). Next, at step 635, the P-wave vector may be tracked by comparing the total magnitude, elevation angle or azimuth angle, individually or in any combination, to previously recorded P-wave data. Alternatively, the present P-wave data may be compared to a reference threshold value or values. An alarm may be generated if an inter-atrial block condition is worsening based on the comparison of the presently measured P-wave to previously measured P-wave data or to reference values. For example, the alarm may be generated when a rate of change is exceeded or when a particular level is exceeded. The total magnitude, elevation angle, and azimuth angle of the terminal P-wave vector may be stored in memory (640), and the process may return to step 605. Component values or inter-atrial block information may also be stored in memory.

A number of embodiments of the invention have been described. Nevertheless, it will be understood that various modifications may be made without departing from the spirit and scope of the invention. Accordingly, other embodiments are within the scope of the following claims.

What is claimed is:

1. A system for monitoring disease status of a patient, comprising:
    a first electrode, a second electrode, and a third electrode, each of the electrodes adapted for implantation in a human being, wherein the first electrode and the second electrode comprise a first pair of electrodes, and wherein the second electrode and the third electrode comprise a second pair of electrodes;
    a voltage measurement circuit configured to measure a first voltage between the first electrode and the second electrode, and to measure a second voltage between the second electrode and the third electrode;
    a memory unit that stores directional information comprising an angle between a first orientation defined by the first pair of electrodes and a second orientation defined by the second pair of electrodes; and
    a processing unit configured to:
    1) calculate, using the stored directional information and the measured first and second voltages, a first resultant vector comprising a magnitude and a direction;
    2) calculate a vectorial difference between the first resultant vector and a second resultant vector, the second resultant vector having been previously calculated by the processing unit using the stored directional information and a previously measured third voltage between the first electrode and the second electrode and a previously measured fourth voltage between the second electrode and the third electrode; and 3) determine a disease status for the patient based on the calculated vectorial difference, and generate an alarm if the calculated vectorial difference satisfies a predetermined criterion.

2. The system of claim 1, wherein the disease status determination is a detection of an inter-atrial block condition.

3. The system of claim 1, wherein the first voltage and the second voltage are representative of a portion of an electrical P-wave cardiac signal associated with activation of a left atrium of a heart.

4. A method of monitoring cardiac pathologies in a human being, the method comprising:

measuring a first voltage between a first electrode and a second electrode and measuring a second voltage between the second electrode and a third electrode, wherein the first electrode and the second electrode comprise a first pair of electrodes, and wherein the second electrode and the third electrode comprise a second pair of electrodes;

calculating, using directional information that comprises an angle between a first orientation defined by the first pair of electrodes and a second orientation defined by the second pair of electrodes and using the measured first and second voltages, a first resultant vector comprising a magnitude and a direction;

calculating a vectorial difference between the first resultant vector and a second resultant vector, the second resultant vector having been previously calculated using the directional information and a previously measured third voltage between the first electrode and the second electrode and a previously measured fourth voltage between the second electrode and the third electrode; and determining a disease status for the patient based on the calculated vectorial difference, and generating an alarm if the calculated vectorial difference satisfies a predetermined criterion.

5. A method of detecting fluid decompensation in a human being, the method comprising:

implanting a first electrode, a second electrode, and a third electrode within the human being, wherein the first electrode and the second electrode comprise a first pair of electrodes, and wherein the second electrode and the third electrode comprise a second pair of electrodes;

measuring a first voltage between the first electrode and the second electrode, and measuring a second voltage between the second electrode and the third electrode;

calculating, using directional information that comprises an angle between a first orientation defined by the first pair of electrodes and a second orientation defined by the second pair of electrodes and using the measured first and second voltages, a first resultant vector comprising a magnitude and a direction;

calculating a vectorial difference between the first resultant vector and a second resultant vector, the second resultant vector having been previously calculated using the directional information and a previously measured third voltage between the first electrode and the second electrode and a previously measured fourth voltage between the second electrode and the third electrode; and determining a degree of fluid decompensation for the patient based on the calculated vectorial difference, and generating an alarm if the calculated vectorial difference satisfies a predetermined criterion.

6. The method of claim 5, wherein determining the degree of fluid decompensation comprises tracking a magnitude of the calculated vectorial difference.

7. The method of claim 5, wherein determining the degree of fluid decompensation comprises tracking a direction of the calculated vectorial difference.

8. A system for monitoring disease status of a patient, comprising:

a first electrode, a second electrode, a third electrode, and a fourth electrode, each of the electrodes adapted for implantation in a human being, wherein the first electrode and the second electrode comprise a first pair of electrodes, and wherein the third electrode and the fourth electrode comprise a second pair of electrodes;

a voltage measurement circuit configured to measure a first voltage between the first electrode and the second electrode, and to measure a second voltage between the third electrode and the fourth electrode;

a memory unit that stores directional information comprising an angle between a first orientation defined by the first pair of electrodes and a second orientation defined by the second pair of electrodes; and a processing unit configured to:

1) calculate, using the stored directional information and the measured first and second voltages, a first resultant vector comprising a magnitude and a direction;

2) calculate a vectorial difference between the first resultant vector and a second resultant vector, the second resultant vector having been previously calculated by the processing unit using the stored directional information and a previously measured third voltage between the first electrode and the second electrode and a previously measured fourth voltage between the third electrode and the fourth electrode; and 3) determine a disease status for the patient based on the calculated vectorial difference, and generate an alarm if the calculated vectorial difference satisfies a predetermined criterion.

9. The system of claim 8, wherein the first voltage and the second voltage are representative of a portion of an electrical P-wave cardiac signal associated with activation of a left atrium of a heart.

10. The system of claim 8, wherein the processing unit detects, using measurements from the voltage measurement circuit: i) a first measurement associated with a P-wave onset feature and a second measurement associated with a P-wave offset feature; ii) a third measurement associated with a first midpoint that is midway in time between the first measurement and the second measurement; and iii) a fourth measurement associated with a second midpoint that is midway in time between the second measurement and the third measurement; and wherein the fourth measurement is a voltage representative of a portion of an electrical P-wave cardiac signal associated with an activation of a left atrium of a heart.

* * * * *